(12) United States Patent
Sconzert et al.

(10) Patent No.: US 11,632,015 B2
(45) Date of Patent: Apr. 18, 2023

(54) AXIAL FLUX MOTOR FOR PERCUTANEOUS CIRCULATORY SUPPORT DEVICE

(71) Applicant: Boston Scientific Scimed Inc., Maple Grove, MN (US)

(72) Inventors: Kalyna L. Sconzert, Minneapolis, MN (US); Joseph A. Kronstedt, New Hope, MN (US); Benjamin Breidall, Eden Prairie, MN (US); Kimberly A. Robertson, Forest Lake, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 257 days.

(21) Appl. No.: 16/552,659

(22) Filed: Aug. 27, 2019

(65) Prior Publication Data

US 2020/0076271 A1 Mar. 5, 2020

Related U.S. Application Data

(60) Provisional application No. 62/723,591, filed on Aug. 28, 2018.

(51) Int. Cl.
*H02K 7/08* (2006.01)
*H02K 16/00* (2006.01)
(Continued)

(52) U.S. Cl.
CPC ............... *H02K 7/08* (2013.01); *H02K 1/165* (2013.01); *H02K 3/12* (2013.01); *H02K 3/26* (2013.01);
(Continued)

(58) Field of Classification Search
CPC ........ H02K 16/00; H02K 1/165; H02K 21/24; H02K 3/12; H02K 3/26; H02K 3/28;
(Continued)

(56) References Cited

U.S. PATENT DOCUMENTS 1,947,269 A   2/1934 Leibing
4,570,093 A * 2/1986 Morii ...................... H02K 7/20
                                                    310/154.43

(Continued)

FOREIGN PATENT DOCUMENTS

EP   1135181 B1   1/2007
EP   3222301 A1   9/2017
(Continued)

OTHER PUBLICATIONS

International Search Report and Written Opinion issued in PCT/US2019/048350, dated Nov. 25, 2019, 15 pages.

*Primary Examiner* — Alex W Mok
(74) *Attorney, Agent, or Firm* — Faegre Drinker Biddle & Reath LLP

(57) ABSTRACT

An axial flux motor includes a housing; a drive shaft disposed within the housing; at least one rotor; and at least one stator. The at least one rotor includes a diametrically-magnetized single pole pair magnetic ring having a rotor aperture defined through the center of the magnetic ring, where the drive shaft extends through the rotor aperture and where the at least one rotor is fixed to the drive shaft. The at least one stator includes a number of conductive windings and a stator aperture, where the drive shaft extends through the stator aperture and where the drive shaft is rotatable within the aperture. The at least one stator is configured to generate an axial magnetic field that causes the at least one rotor to rotate, thereby rotating the drive shaft.

15 Claims, 6 Drawing Sheets

(51) Int. Cl.
*H02K 3/26* (2006.01)
*H02K 3/28* (2006.01)
*H02K 3/48* (2006.01)
*H02K 3/12* (2006.01)
*H02K 1/16* (2006.01)
*H02K 7/00* (2006.01)

(52) U.S. Cl.
CPC ............... *H02K 3/28* (2013.01); *H02K 3/48* (2013.01); *H02K 7/003* (2013.01); *H02K 16/00* (2013.01)

(58) Field of Classification Search
CPC .... H02K 3/47; H02K 3/48; H02K 7/003; H02K 7/08
USPC .......................................................... 310/90
See application file for complete search history.

(56) References Cited

U.S. PATENT DOCUMENTS

| | | | | |
|---|---|---|---|---|
| 5,205,721 | A * | 4/1993 | Isaacson | A61M 60/422 417/356 |
| 5,722,930 | A | 3/1998 | Larson et al. | |
| 5,911,685 | A * | 6/1999 | Siess | H02K 5/132 600/16 |
| 6,037,696 | A * | 3/2000 | Sromin | H02K 1/2793 310/112 |
| 6,264,601 | B1 * | 7/2001 | Jassawalla | F04B 43/04 600/16 |
| 6,320,290 | B1 * | 11/2001 | Kanebako | H02K 7/09 310/90.5 |
| 6,897,595 | B1 | 5/2005 | Chiarenza | |
| 7,798,952 | B2 | 9/2010 | Tansley et al. | |
| 8,177,703 | B2 | 5/2012 | Smith et al. | |
| 8,299,676 | B2 * | 10/2012 | Miyata | H02K 3/47 310/208 |
| 9,370,613 | B2 | 6/2016 | Hsu et al. | |
| 2004/0090134 | A1 * | 5/2004 | Ide | H02K 19/38 310/112 |
| 2005/0135948 | A1 * | 6/2005 | Olsen | F16C 32/0461 417/423.12 |
| 2006/0028081 | A1 * | 2/2006 | Minagawa | H02K 16/00 310/156.36 |
| 2006/0033393 | A1 * | 2/2006 | Ritchey | H02K 7/108 310/112 |
| 2006/0279876 | A1 * | 12/2006 | Albrecht | G11B 33/12 |
| 2007/0156006 | A1 | 7/2007 | Smith et al. | |
| 2007/0241634 | A1 * | 10/2007 | Tenhunen | H02K 29/03 310/268 |
| 2007/0276480 | A1 | 11/2007 | Tansley et al. | |
| 2008/0024035 | A1 * | 1/2008 | Aydin | B60K 6/26 310/268 |
| 2009/0001831 | A1 * | 1/2009 | Cho | H02K 7/09 310/112 |
| 2010/0019589 | A1 * | 1/2010 | Saban | H02K 3/12 310/52 |
| 2010/0266423 | A1 | 10/2010 | Gohean et al. | |
| 2012/0223600 | A1 * | 9/2012 | Tonogi | H02K 1/148 310/46 |
| 2014/0191606 | A1 * | 7/2014 | Gieras | H02K 16/00 310/112 |
| 2015/0031936 | A1 * | 1/2015 | LaRose | A61M 60/196 600/16 |
| 2015/0084446 | A1 | 3/2015 | Atar | |
| 2015/0141739 | A1 | 5/2015 | Hsu et al. | |

FOREIGN PATENT DOCUMENTS

| | | |
|---|---|---|
| EP | 3319098 A1 | 5/2018 |
| JP | 2001-078389 A | 3/2001 |
| JP | 2018-082610 A | 5/2018 |
| JP | 2018-093617 A | 6/2018 |
| WO | 2008/117631 A1 | 10/2008 |
| WO | 2016/125313 A1 | 8/2016 |
| WO | 2017/162619 A1 | 9/2017 |
| WO | 2020/046940 A1 | 3/2020 |

\* cited by examiner

AXIAL FLUX MOTOR FOR PERCUTANEOUS CIRCULATORY SUPPORT DEVICE

CROSS REFERENCE TO RELATED APPLICATION

This application claims priority to Provisional Application No. 62/723,591, filed Aug. 28, 2018, which is herein incorporated by reference in its entirety.

TECHNICAL FIELD

The present disclosure relates to magnetic motors. More specifically, the disclosure relates to percutaneous circulatory support devices having axial flux magnetic motors.

BACKGROUND

Heart Failure occurs when the heart is unable to pump enough blood to meet the metabolic needs of the body. It is the leading cause of hospitalization for patients older than 65 years of age, has a 3 year mortality rate of 50%, and has cost the healthcare system over $30 billion. Potential solutions to treat heart failure patients include percutaneous mechanical circulatory support—a way to provide acute partial support percutaneously, thus increasing cardiac output as desired. Percutaneous circulatory support may be used in patients presenting with Acute Decompensated Heart Failure (ADHF), cardiogenic shock, and/or during high-risk PCI procedures.

SUMMARY

In an Example 1, an axial flux motor comprises: a housing; a drive shaft disposed within the housing; at least one rotor, the at least one rotor comprising a diametrically-magnetized single pole pair magnetic ring having a rotor aperture defined through the center of the magnetic ring, wherein the drive shaft extends through the rotor aperture and wherein the at least one rotor is fixed to the drive shaft; and at least one stator, the at least one stator comprising a plurality of conductive windings and a stator aperture, wherein the drive shaft extends through the stator aperture and wherein the drive shaft is rotatable within the aperture, and wherein the at least one stator is configured to generate an axial magnetic field that causes the at least one rotor to rotate, thereby rotating the drive shaft.

In an Example 2, the motor of Example 1, the at least one stator comprising a plurality of stators, wherein each of the plurality of stators is configured to cause at least one adjacent rotor to rotate.

In an Example 3, the motor of either of Examples 1 or 2, the at least one stator comprising a slotted stator core, wherein each of the plurality of conductive windings is wound around one or more slots of the stator core.

In an Example 4, the motor of any of Examples 1-3, wherein each of the windings is approximately wedge-shaped, having a first width at a first end, adjacent the drive shaft, and a second width at a second end, wherein the second width is greater than the first width.

In an Example 5, the motor of any of Examples 1-4, further comprising: a first bearing rotatably coupled to the drive shaft; a second bearing rotatably coupled to the drive shaft, such that the at least one rotor and the at least one stator are disposed between the first bearing and the second bearing; a first flux return disc disposed between the first bearing and the at least one rotor and the at least one stator; and a second flux return disc disposed between the second bearing and the at least one rotor and the at least one stator.

In an Example 6, the motor of Example 5, wherein each of the first and second flux return discs is made of a Hiperco alloy.

In an Example 7, the motor of any of Examples 1-6, wherein each of the plurality of windings is printed on a printed circuit board or 3D printed.

In an Example 8, the motor of any of Examples 1-7, wherein the motor is configured to drive an impeller of a percutaneous mechanical circulatory support device, wherein the impeller is coupled to the drive shaft.

In an Example 9, an axial flux motor comprises: a housing; a drive shaft disposed within the housing; at least one rotor, the at least one rotor comprising a diametrically-magnetized single pole pair magnetic ring having a rotor aperture defined through the center of the magnetic ring, wherein the drive shaft extends through the rotor aperture and wherein the at least one rotor is fixed to the drive shaft; and at least one stator, the at least one stator comprising a plurality of conductive windings arranged around the drive shaft and a stator aperture, wherein the drive shaft extends through the stator aperture and wherein the drive shaft is rotatable within the aperture, wherein the at least one stator does not include a stator core, and wherein the at least one stator is configured to generate an axial magnetic field that causes the at least one rotor to rotate, thereby rotating the drive shaft.

In an Example 10, the motor of Example 9, wherein each of the plurality of conductive windings is coupled to an inside surface of the housing, and wherein each of the plurality of windings is approximately wedge-shaped, having a first width at a first end, adjacent the drive shaft, and a second width at a second end, and wherein the second width is greater than the first width.

In an Example 11, the motor of either of Examples 9 or 10, wherein each of the plurality of windings is 3D printed.

In an Example 12, the motor of any of Examples 9-11, further comprising: a first bearing rotatably coupled to the drive shaft; a second bearing rotatably coupled to the drive shaft, such that the at least one rotor and the at least one stator are disposed between the first bearing and the second bearing; a first Hiperco alloy flux return disc disposed between the first bearing and the at least one rotor and the at least one stator; and a second Hiperco alloy flux return disc disposed between the second bearing and the at least one rotor and the at least one stator.

In an Example 13, the motor of any of Examples 9-12, wherein the motor is configured to drive an impeller of a percutaneous mechanical circulatory support device, wherein the impeller is coupled to the drive shaft.

In an Example 14, a percutaneous mechanical circulatory support device comprises: a housing; a drive shaft disposed within the housing; a plurality of rotors, each of the plurality of rotors comprising a diametrically-magnetized single pole pair magnetic ring having a rotor aperture defined through the center of the magnetic ring, wherein the drive shaft extends through the rotor aperture and wherein the rotor is fixed to the drive shaft; and a plurality of stators, each stator of the plurality of stators comprising a plurality of conductive windings and a stator aperture, wherein the drive shaft extends through the stator aperture and wherein the drive shaft is rotatable within the aperture, and wherein each stator of the plurality of stators is configured to generate an axial magnetic field that causes at least one adjacent rotor of the plurality of rotors to rotate, thereby rotating the drive shaft.

In an Example 15, the circulatory support device of Example 14, further comprising a controller operably coupled to the motor and configured to: activate, during a startup procedure, the plurality of stators; and deactivate, upon determining that the motor has a specified operating condition, one or more of the plurality of stators.

In an Example 16, an axial flux motor, comprises: a housing; a drive shaft disposed within the housing; at least one rotor, the at least one rotor comprising a diametrically-magnetized single pole pair magnetic ring having a rotor aperture defined through the center of the magnetic ring, wherein the drive shaft extends through the rotor aperture and wherein the at least one rotor is fixed to the drive shaft; and at least one stator, the at least one stator comprising a plurality of conductive windings and a stator aperture, wherein the drive shaft extends through the stator aperture and wherein the drive shaft is rotatable within the aperture, and wherein the at least one stator is configured to generate an axial magnetic field that causes the at least one rotor to rotate, thereby rotating the drive shaft.

In an Example 17, the motor of Example 16, the at least one stator comprising a plurality of stators, wherein each of the plurality of stators is configured to cause at least one adjacent rotor to rotate.

In an Example 18, the motor of Example 16, the at least one stator comprising a slotted stator core, wherein each of the plurality of conductive windings is wound around one or more slots of the stator core.

In an Example 19, the motor of Example 16, wherein each of the windings is approximately wedge-shaped, having a first width at a first end, adjacent the drive shaft, and a second width at a second end, wherein the second width is greater than the first width.

In an Example 20, the motor of Example 16, further comprising: a first bearing rotatably coupled to the drive shaft; a second bearing rotatably coupled to the drive shaft, such that the at least one rotor and the at least one stator are disposed between the first bearing and the second bearing; a first flux return disc disposed between the first bearing and the at least one rotor and the at least one stator; and a second flux return disc disposed between the second bearing and the at least one rotor and the at least one stator.

In an Example 21, the motor of Example 20, wherein each of the first and second flux return discs is made of a Hiperco alloy.

In an Example 22, the motor of Example 16, wherein each of the plurality of windings is printed on a printed circuit board or 3D printed.

In an Example 23, the motor of Example 16, wherein the motor is configured to drive an impeller of a percutaneous mechanical circulatory support device, wherein the impeller is coupled to the drive shaft.

In an Example 24, an axial flux motor comprises: a housing; a drive shaft disposed within the housing; at least one rotor, the at least one rotor comprising a diametrically-magnetized single pole pair magnetic ring having a rotor aperture defined through the center of the magnetic ring, wherein the drive shaft extends through the rotor aperture and wherein the at least one rotor is fixed to the drive shaft; and at least one stator, the at least one stator comprising a plurality of conductive windings arranged around the drive shaft and a stator aperture, wherein the drive shaft extends through the stator aperture and wherein the drive shaft is rotatable within the aperture, wherein the at least one stator does not include a stator core, and wherein the at least one stator is configured to generate an axial magnetic field that causes the at least one rotor to rotate, thereby rotating the drive shaft.

In an Example 25, the motor of Example 24, wherein each of the plurality of conductive windings is coupled to an inside surface of the housing.

In an Example 26, the motor of Example 24, wherein each of the plurality of windings is approximately wedge-shaped, having a first width at a first end, adjacent the drive shaft, and a second width at a second end, and wherein the second width is greater than the first width.

In an Example 27, the motor of Example 24, further comprising: a first bearing rotatably coupled to the drive shaft; a second bearing rotatably coupled to the drive shaft, such that the at least one rotor and the at least one stator are disposed between the first bearing and the second bearing; a first Hiperco alloy flux return disc disposed between the first bearing and the at least one rotor and the at least one stator; and a second Hiperco alloy flux return disc disposed between the second bearing and the at least one rotor and the at least one stator.

In an Example 28, the motor of Example 24, wherein the motor is configured to drive an impeller of a percutaneous mechanical circulatory support device, wherein the impeller is coupled to the drive shaft.

In an Example 29, a percutaneous mechanical circulatory support device, comprises: a housing; a drive shaft disposed within the housing; a plurality of rotors, each of the plurality of rotors comprising a diametrically-magnetized single pole pair magnetic ring having a rotor aperture defined through the center of the magnetic ring, wherein the drive shaft extends through the rotor aperture and wherein the rotor is fixed to the drive shaft; and a plurality of stators, each stator of the plurality of stators comprising a plurality of conductive windings and a stator aperture, wherein the drive shaft extends through the stator aperture and wherein the drive shaft is rotatable within the aperture, and wherein each stator of the plurality of stators is configured to generate an axial magnetic field that causes at least one adjacent rotor of the plurality of rotors to rotate, thereby rotating the drive shaft.

In an Example 30, the circulatory support device of Example 29, further comprising a controller operably coupled to the motor and configured to: activate, during a startup procedure, the plurality of stators; and deactivate, upon determining that the motor has a specified operating condition, one or more of the plurality of stators.

In an Example 31, the motor of Example 29, further comprising: a first bearing rotatably coupled to the drive shaft; a second bearing rotatably coupled to the drive shaft, such that the plurality of rotors and the plurality of stators are disposed between the first bearing and the second bearing; a first Hiperco alloy flux return disc disposed between the first bearing and the plurality of rotors and the plurality of stators; and a second Hiperco alloy flux return disc disposed between the second bearing and the plurality of rotors and the plurality of stators.

In an Example 32, the motor of Example 29, the stator comprising a slotted stator core, wherein each of the plurality of conductive windings is wound around one or more slots of the stator core.

In an Example 33, the motor of Example 29, wherein the stator does not include a stator core, and wherein each of the plurality of conductive windings is coupled to an inside surface of the housing.

In an Example 34, the motor of Example 29, wherein each of the windings is approximately wedge-shaped, having a first width at a first end, adjacent the drive shaft, and a second width at a second end, wherein the second width is greater than the first width.

In an Example 35, the motor of Example 29, wherein each of the plurality of windings is printed on a printed circuit board or 3D printed.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

Figure 1:
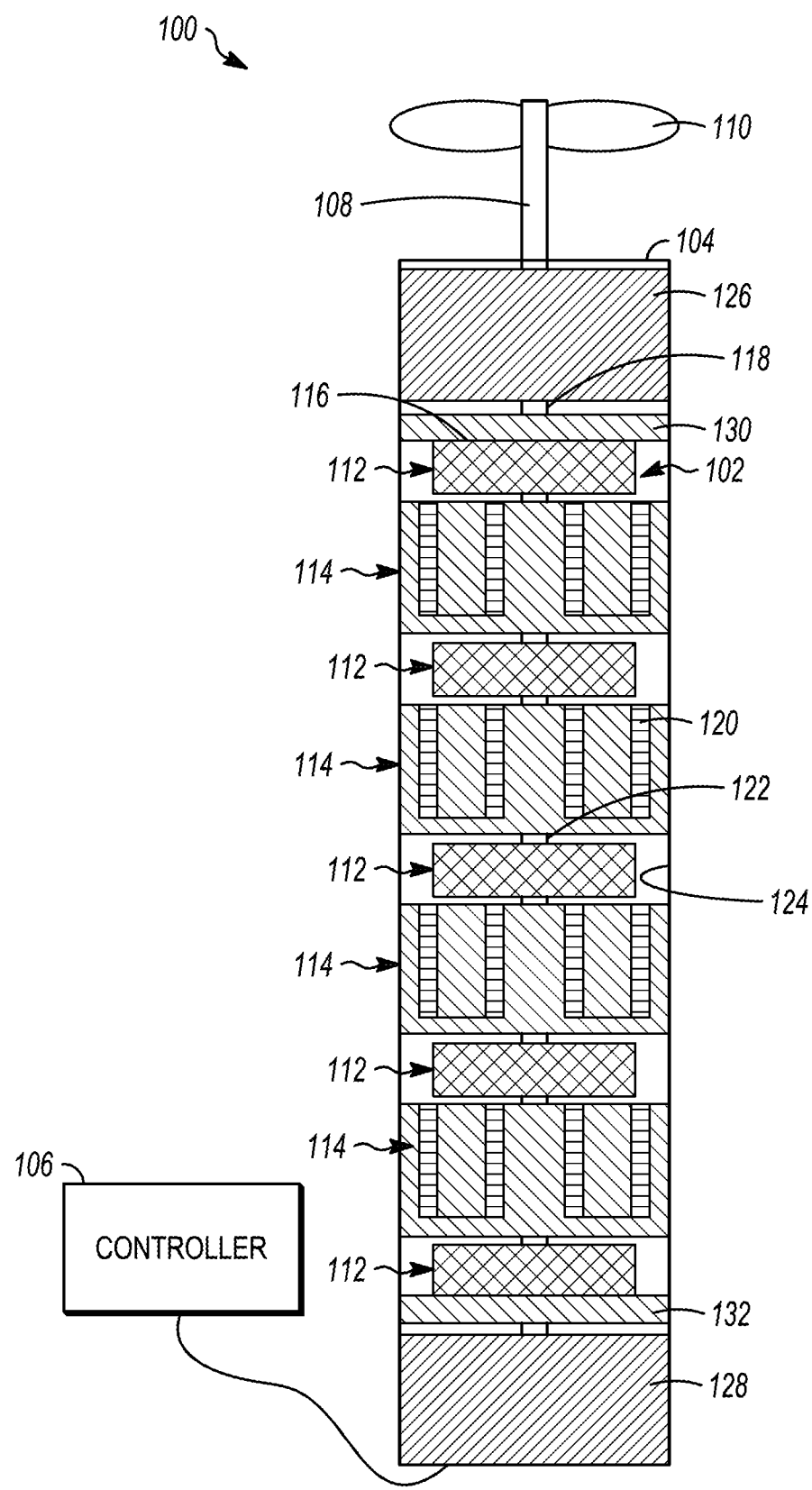
FIG. 1 depicts a cross-sectional side view of an illustrative percutaneous mechanical circulatory support device, in accordance with embodiments of the subject matter disclosed herein.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

The terms "up," "upper," and "upward," and variations thereof, are used throughout this disclosure for the sole purpose of clarity of description and are only intended to refer to a relative direction (i.e., a certain direction that is to be distinguished from another direction), and are not meant to be interpreted to mean an absolute direction. Similarly, the terms "down," "lower," and "downward," and variations thereof, are used throughout this disclosure for the sole purpose of clarity of description and are only intended to refer to a relative direction that is at least approximately opposite a direction referred to by one or more of the terms "up," "upper," and "upward," and variations thereof.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

Axial flux motors differ from the more common radial flux motors due to the direction of magnetic flux in each motor. In radial flux motors, magnetic flux is produced radially along the side of the motor, whereas, in axial flux motors, magnetic flux is produced axially along the axial length of the motor. Axial flux motors generally can be made thinner and lighter with a higher torque-to-weight ratio than radial flux motors. Embodiments described herein include a "multi-stage" axial flux motor, where multiple rotors and stators are stacked axially in order to increase torque in the setting of a limited outer diameter. Embodiments of the axial flux motor disclosed herein may also be customized by connecting the rotor/stator pairs in series, in parallel, and/or in any number of combinations. This ability to arrange the rotor/stator pairs in such ways adds redundancy to the motor and/or may allow deactivation of one or more stators once the motor is running, thereby conserving energy.

FIG. 1 depicts a cross-sectional side view of an illustrative percutaneous mechanical circulatory support device 100, in accordance with embodiments of the subject matter disclosed herein. As shown, the circulatory support device 100 includes an axial flux motor 102 disposed within a housing 104. A controller 106 is operably coupled to the motor 102 and is configured to control the motor 102. The controller 106 may be disposed within the housing 104 in embodiments, or, in other embodiments, may be disposed outside the housing (e.g., in a catheter handle, independent housing, etc.). In embodiments, the controller 106 may include multiple components, one or more of which may be disposed within the housing 104.

According to embodiments, the controller 106 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. Although the controller 106 is referred to herein in the singular, the controller 106 may be implemented in multiple instances, distributed across multiple computing devices, instantiated within multiple virtual machines, and/or the like.

A computing device may include any type of computing device suitable for implementing aspects of embodiments of the disclosed subject matter. Examples of computing devices include specialized computing devices or general-purpose computing devices such as "control units," "control assemblies," "workstations," "servers," "hand-held devices," "controllers," and the like, all of which are contemplated within the scope of FIG. 1, with reference to the controller 106.

In embodiments, a computing device includes a bus that, directly and/or indirectly, couples the following devices: a processing unit, a memory, an input/output (I/O) port, an I/O component, and a power supply. Any number of additional components, different components, and/or combinations of components may also be included in the computing device. The I/O component may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The bus represents what may be one or more busses (such as, for example, an address bus, data bus, or combination thereof). Similarly, in embodiments, the computing device may include a number of processing units, a number of memory components, a number of I/O ports, a number of I/O components, and/or a number of power supplies. Additionally any number of these components, or combinations thereof, may be distributed and/or duplicated across a number of computing devices.

In embodiments, the memory includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

The computer-executable instructions may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware.

As shown in FIG. 1, the motor 102 includes a drive shaft 108 disposed at least partially within the housing 104, and is configured to drive, via rotation of the drive shaft 108, an impeller 110 coupled to the drive shaft 108. In embodiments, the drive shaft 108 may be made of any number of different rigid materials such as, for example, steel, titanium alloys, cobalt chromium alloys, nitinol, high-strength ceramics, and/or the like. According to embodiments, although the motor 102 depicted in FIG. 1 (as well as is described in accordance with various embodiments throughout this disclosure) is depicted as being configured to drive an impeller of a percutaneous mechanical circulatory support device, embodiments of the motor 102 described herein may be configured to be used in implementations other than that of a percutaneous mechanical circulatory support device. For example, embodiments of motors described herein may be implemented in dental tools, insulin pumps, vascular imaging devices, ultrasound probes, atherectomy devices, and/or the like.

As is further shown in FIG. 1, the motor 102 includes a number of rotors 112 and a number of stators 114. Each stator 114 is configured to generate an axial magnetic field that causes one or more adjacent rotors 112 to rotate, thereby rotating the drive shaft 108. According to embodiments, the motor 102 may include any number of rotors and stators, in any combination. For example, the motor 102 may include one stator and two rotors, two stators and one rotor, two stators and two rotors, two stators and three rotors, and/or the like. In embodiments, the stators and rotors may be grouped in pairs (e.g., each stator drives one rotor), adjacent sets of two or three (e.g., each stator drives one rotor or two rotors), and/or the like. In embodiments, the controller 106 may be configured to selectively activate any number of stators according to any number of different polarization patterns and, thereby, drive selected rotors in selected directions.

In embodiments, each of the rotors 112 includes a diametrically-magnetized single pole pair magnetic ring 116 having a rotor aperture 118 defined through the center of the magnetic ring 116. A single pole pair magnetic ring is a magnetic ring having a single pole pair—that is, having a pair of poles (e.g., north and south). According to embodiments, a rotor may include multiple pole pairs, a Hallbach array, and/or the like. The drive shaft 108 extends through the rotor apertures 118 and each of the rotors 112 is fixed to the drive shaft 108. According to embodiments, each rotor may have a diameter of between approximately 3 millimeters (mm) and approximately 4 mm, and may have a thickness of between approximately 0.5 mm and approximately 1.5 mm. In embodiments including percutaneous implementation, a rotor may have a diameter of between approximately 1 mm and approximately 8 mm, and a thickness of between approximately 0.25 mm and approximately 5 mm. In embodiments, a rotor may have a diameter of between approximately 0.5 mm and approximately 20 mm, and a thickness of between approximately 0.1 mm and approximately 8 mm. Each rotor may be formed from any number of different types of magnetic materials such as, for example rare earth magnetic materials (e.g., neodymium, samarium cobalt, etc.), ferrite magnets, and/or the like. According to embodiments, a rotor may be just a ring magnet, while, in other embodiments, the rotor may include the magnet mounted on an alloy core (e.g., a Hiperco alloy core).

According to embodiments, each stator 114 includes a number of conductive windings 120 and a stator aperture 122. The drive shaft 108 extends through each stator aperture 122 and is rotatable within each aperture 122. Each stator 114 is coupled to an inside surface 124 of the housing 104 and is configured to generate an axial magnetic field that causes at least one adjacent rotor 112 to rotate, thereby rotating the drive shaft 108. According to embodiments, the windings of a stator are energized in phases, creating an electromagnet. In embodiments, the windings may include any number of different types of electrical wire such as, for example, copper magnetic wires, silver-coated copper wires, gold wires, aluminum wires, copper-coated steels wires, graphene wires, and/or the like. In embodiments, the wires may be any number of different sizes. One illustrative, but non-limiting, wire size may be 36 AWG.

According to embodiments, the windings 120 may be configured according to any number of different shapes, sizes, and/or the like. The windings 120 may be attached to a stator core and/or other windings to create a stator. For example, in embodiments, windings may be deposited in slots in a stator core, wound around posts on a stator core, and/or the like. In embodiments, the stator may be a printed circuit board on which the windings are printed. Windings printed on a circuit board may be printed in any number of different patterns, sizes, depths, and/or the like. In embodiments, windings may be printed using a three-dimensional (3D) printer. Any number of different manufacturing techniques may be used to create windings.

Figure 2:
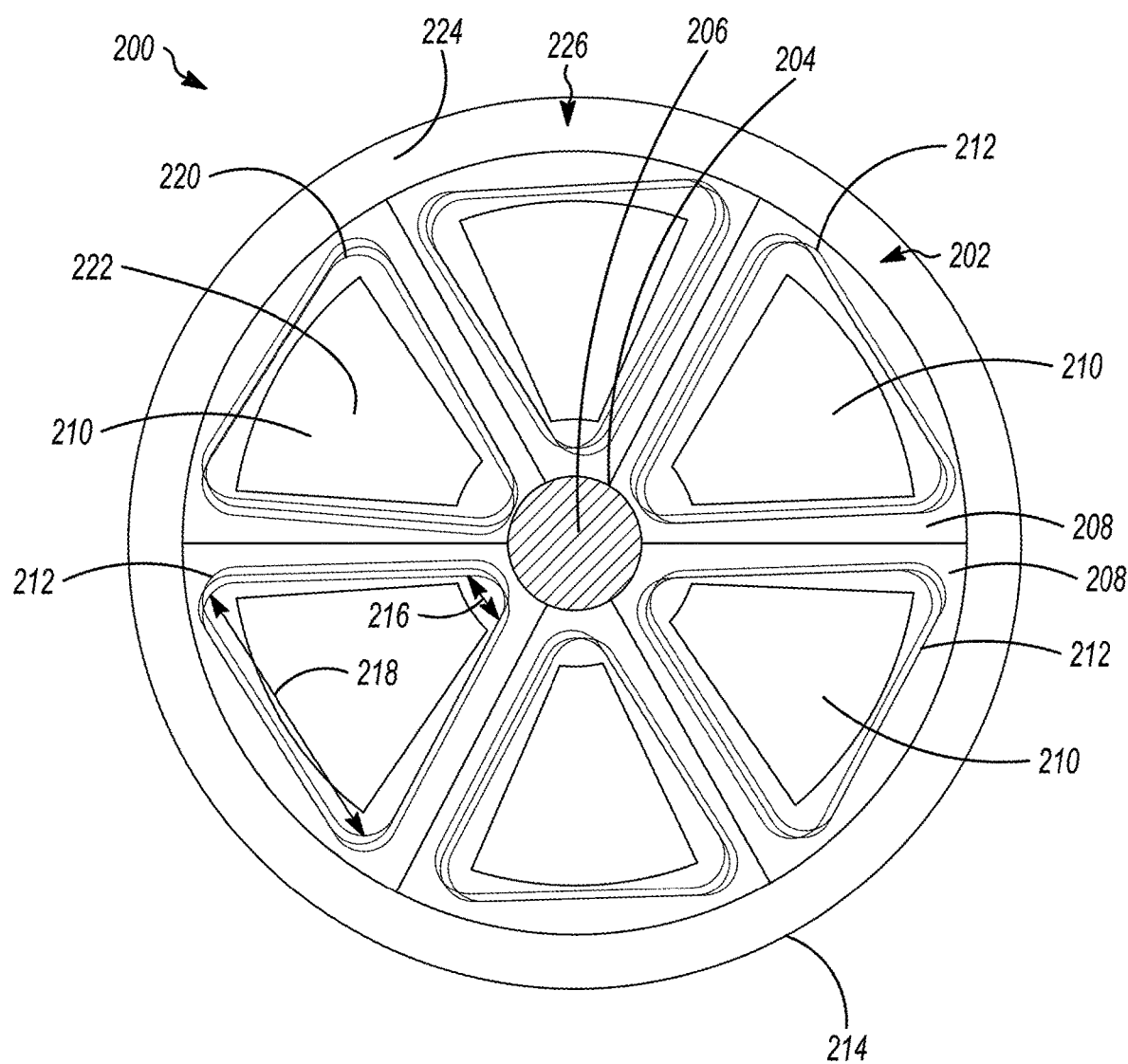
FIG. 2 depicts a top-view of an illustrative stator, having a stator core, in accordance with embodiments of the subject matter disclosed herein.

As indicated above, the windings 120 may be configured according to any number of different shapes. For example, each winding of a stator may be approximately wedge-shaped, thereby maximizing volume available for the winding in a cylindrical motor housing. FIG. 2 depicts a top-view of an illustrative stator 200, in accordance with embodiments of the subject matter disclosed herein. According to embodiments, the stator 200 may be, or be similar to, any one or more of the stators 114 depicted in FIG. 1. As shown, the stator 200 includes a stator core 202, which may be made of an alloy such as, for example, a Hiperco alloy. The stator core 202 may include a stator aperture 204 through which a drive shaft 206 is rotatably disposed. According to embodiments, the stator core 202 may include a diameter of between approximately 3 mm and approximately 4 mm, and may include a thickness (e.g., in the axial dimension) of between approximately 2 mm and approximately 3 mm. In embodiments, the stator core 202 may include a diameter of between approximately 1 mm and approximately 8 mm, and may include a thickness (e.g., in the axial dimension) of between approximately 0.25 mm and approximately 5 mm. In embodiments, the stator core 202 may have a diameter of between approximately 0.5 mm and approximately 20 mm, and a thickness of between approximately 0.1 mm and approximately 8 mm.

The stator core 202 may also include slots 208, forming teeth 210 around which the windings 212 may be wound. In embodiments, the stator core 202 may be slotless, in which case, the windings 212 may be wound along the face 214 of the stator core 202. As shown in FIG. 2, each of the windings 212 disposed in a slotted stator core 202 may be approximately wedge-shaped. That is, each winding 212 may have a first width 216 at a first end (adjacent the drive shaft 206), and a second width 218 at a second end (adjacent an inside surface of the motor housing (not shown)), wherein the second width 218 is wider than the first width 216. According to embodiments, each winding 212 may be wound such that an upper end 220 of the winding is approximately flush with an upper surface 222 of the tooth 210 around which it is wound. In embodiments, an upper surface 224 of an outer edge 226 of the stator core 202 may also be approximately flush with the upper end 220 of the winding 212 and the upper surface 222 of the tooth 210.

With continued reference to FIG. 1, the motor 102 may further include a first bearing 126 rotatably coupled to the drive shaft 108 and a second bearing 128 rotatably coupled to the drive shaft 108, such that the rotors 112 and stators 114 are disposed between the first bearing 126 and the second bearing 128. The first and second bearings 126 and 128 may be any kind of bearings such as, for example, ball bearings, journal bearings, and/or the like. For example, in embodiments, the first bearing 126 may be a ball bearing, while the second bearing 128 is a journal bearing. In other embodiments, the first bearing 126 may be a journal bearing, while the second bearing 128 is a ball bearing. In other embodiments, both bearings 126 and 128 may be ball bearings or journal bearings. According to embodiments, the outer diameter of the bearings 126 and 128 are configured such that the bearings can be coupled to the inside surface 124 of the housing 104, allowing the drive shaft 108 to rotate within the housing 104.

As is further shown in FIG. 1, the motor 102 may further include a first flux return disc 130 disposed between the first bearing 126 and the rotors 112 and the stators 114; and a second flux return disc 132 may be disposed between the second bearing 128 and the rotors 112 and the stators 114. The flux return discs 130 and 132 may be made of any ferromagnetic material that may be used to redirect magnetic flux and, thereby, in embodiments, may be configured to protect the adjacent bearings from magnetic interaction, as well as to focus the magnetic field lines through the adjacent rotor and/or stator, thereby facilitating increasing power and efficiency of the motor 102. In embodiments, for example, each flux return disc 130 and 132 may be made of a Hiperco alloy, any number of different types of steel, iron, and/or the like. Each flux return disc 130 and 132 may, in embodiments, have an outer diameter approximately equal to the outer diameter of the bearings 126 and 128 and the stators 114.

The illustrative circulatory support device 100 and motor 102 shown in FIG. 1, and the illustrative stator 200 shown in FIG. 2, are not intended to suggest any limitation as to the scope of use or functionality of embodiments of the present disclosure. The illustrative circulatory support device 100, motor 102, and stator 200 also should not be interpreted as having any dependency or requirement related to any single component or combination of components illustrated therein. For example, some embodiments may not include flux return discs, while other embodiments may include one or more flux return discs, depending upon magnet types, size constraints, motor configuration, presence of lamination stacks, motor housing material, and/or the like. Additionally, various components depicted in FIGS. 1 and 2 may be, in embodiments, integrated with various ones of the other components depicted therein (and/or components not illustrated), all of which are considered to be within the ambit of the present disclosure.

According to embodiments, an axial flux motor may include stators that do not have stator cores. In such embodiments, the windings are arranged with similar materials, but they are secured to the motor housing. In embodiments, the outer diameter of the windings may be slightly larger than the windings that are provided in a stator with a stator core, as the windings are coupled to the inside surface of the motor housing. For example, the overall diameter of a stator without a stator core may be between approximately 4 mm and 4.5 mm.

Figure 3:
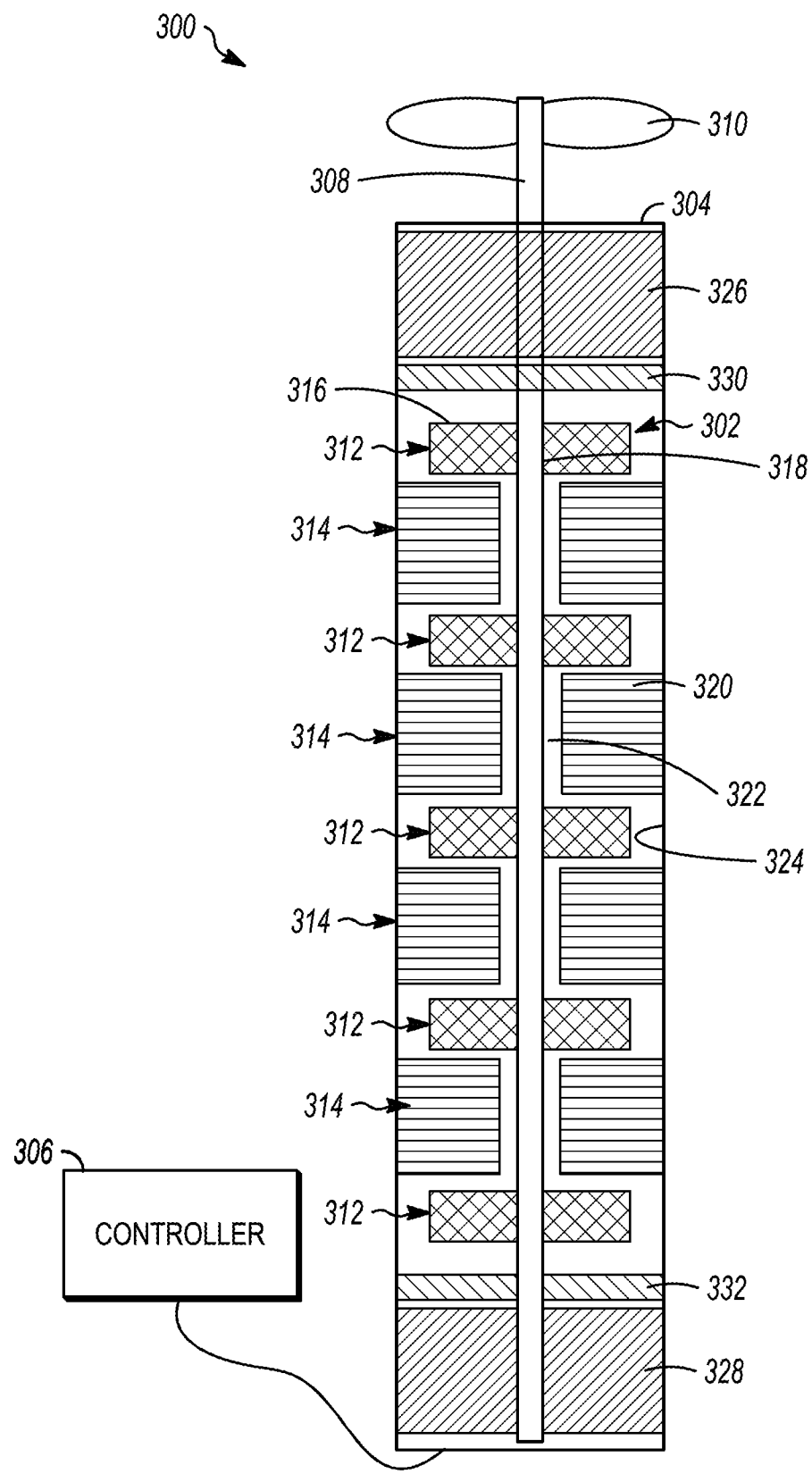
FIG. 3 depicts a cross-sectional side view of an illustrative percutaneous mechanical circulatory support device, in accordance with embodiments of the subject matter disclosed herein, in which stators without stator cores are provided.

FIG. 3 depicts a cross-sectional side view of an illustrative percutaneous mechanical circulatory support device 300, in accordance with embodiments of the subject matter disclosed herein, in which stators without stator cores are provided. According to embodiments, other than the configuration of the stators, the circulatory support device 300, the motor 302, and/or any component thereof, may be the same as, or similar to, corresponding components depicted in FIG. 1. As shown, the circulatory support device 300 includes an axial flux motor 302 disposed within a housing 304. A controller 306 is operably coupled to the motor 302 and is configured to control the motor 302. The controller 306 may be disposed within the housing 304 in embodiments, or, in other embodiments, may be disposed outside the housing (e.g., in a catheter handle, independent housing, etc.). In embodiments, the controller 306 may include multiple components, one or more of which may be disposed within the housing 304.

According to embodiments, the controller 306 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. Although the controller 306 is referred to herein in the singular, the controller 306 may be implemented in multiple instances, distributed across multiple computing devices, instantiated within multiple virtual machines, and/or the like.

As shown in FIG. 3, the motor 302 includes a drive shaft 308 disposed at least partially within the housing 304, and is configured to drive, via rotation of the drive shaft 308, an impeller 310 coupled to the drive shaft 308. According to embodiments, although the motor 302 depicted in FIG. 3 (as well as is described in accordance with various embodiments throughout this disclosure) is depicted as being configured to drive an impeller of a percutaneous mechanical circulatory support device, embodiments of the motor 302 described herein may be configured to be used in implementations other than that of a percutaneous mechanical circulatory support device. For example, embodiments of motors described herein may be implemented in dental tools, insulin pumps, interventional cardiology devices, ultrasound probes, and/or the like.

As is further shown in FIG. 3, the motor 302 includes a number of rotors 312, and a number of stators 314. Each stator is configured to generate an axial magnetic field that causes one or more adjacent rotors to rotate, thereby rotating the drive shaft. According to embodiments, the motor 302 may include any number of stators and rotors. For example, the motor 302 may include one stator and two rotors, two stators and one rotor, two stators and two rotors, two stators and three rotors, and/or the like. In embodiments, the stators and rotors may be grouped in pairs (e.g., each stator drives one rotor), adjacent sets of two or three (e.g., each stator drives one rotor or two rotors), and/or the like. In embodiments, the controller 306 may be configured to selectively activate any number of stators according to any number of different polarization patterns and, thereby, drive selected rotors in selected directions.

Each of the rotors 312 includes a diametrically-magnetized single pole pair magnetic ring 316, having a rotor aperture 318, defined through the center of the magnetic ring 316. The drive shaft 308 extends through the rotor apertures 318 and each of the rotors 312 is fixed to the drive shaft 308. According to embodiments, each rotor may have a diameter of between approximately 3 millimeters (mm) and approximately 4 mm, and may have a thickness of between approximately 0.5 mm and 1.5 mm. Each rotor may be formed from any number of different types of magnetic materials such as, for example neodymium. According to embodiments, a rotor may be just a ring magnet, while, in other embodiments, the rotor may include the magnet mounted on an alloy core (e.g., a Hiperco alloy core).

According to embodiments, each stator 314 includes a number of conductive windings 320 and a stator aperture 322. The drive shaft 308 extends through each stator aperture 322 and is rotatable within each aperture 322. Each stator 314 is coupled to an inside surface 324 of the housing 304 and is configured to generate an axial magnetic field that causes at least one adjacent rotor 312 to rotate, thereby rotating the drive shaft 308. According to embodiments, the windings of a stator are energized in phases, creating an electromagnet. In embodiments, the windings may include any number of different types of wire such as, for example, 36 AWG copper magnet wires.

Figure 4:
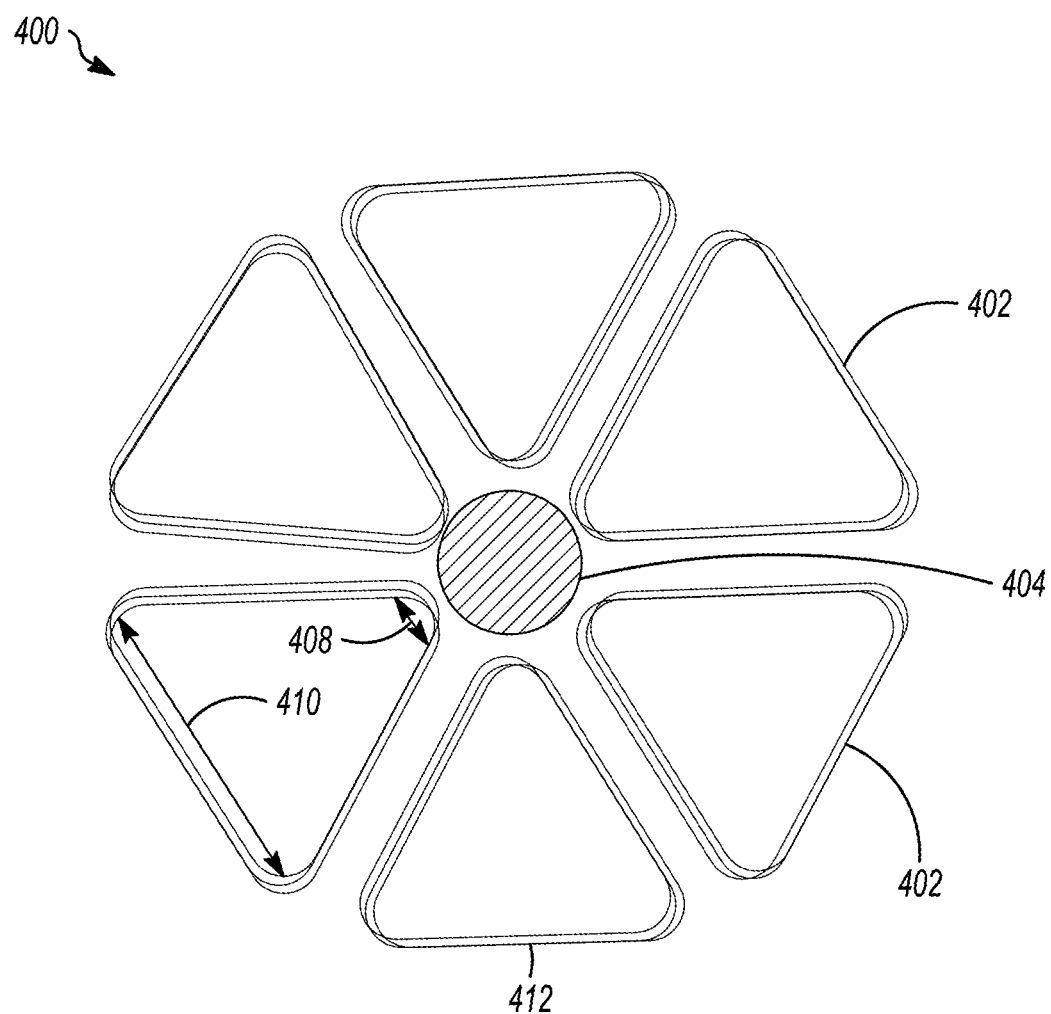
FIG. 4 depicts a cross-sectional top-view of an illustrative stator, without a stator core, in accordance with embodiments of the subject matter disclosed herein.

According to embodiments, the windings may be configured according to any number of different shapes. For example, each winding of a stator may be approximately wedge-shaped, thereby maximizing volume available for the winding in a cylindrical motor housing. FIG. 4 depicts a cross-sectional top-view of an illustrative stator 400, in accordance with embodiments of the subject matter disclosed herein. According to embodiments, the stator 400 may be, or be similar to, any one or more of the stators 314 depicted in FIG. 3. As shown, the stator 400 includes windings 402, that may be approximately wedge-shaped, and that are disposed around a stator aperture 404, within which a drive shaft 406 is configured to rotate. That is, each winding 402 may have a first width 408 at a first end (adjacent the drive shaft 406), and a second width 410 at a second end (adjacent an inside surface of the motor housing (not shown)), wherein the second width 410 is wider than the first width 408. At least a portion of an outer edge 412 of each winding 402 may be configured to be coupled to the inside surface of a motor housing.

With continued reference to FIG. 3, the motor 302 may further include a first bearing 326 rotatably coupled to the drive shaft 308 and a second bearing 328 rotatably coupled to the drive shaft 308, such that the rotors and stators are disposed between the first bearing 326 and the second bearing 328. The first and second bearings 326 and 328 may be any kind of bearings such as, for example, ball bearings, journal bearings, and/or the like. For example, in embodiments, the first bearing 326 may be a ball bearing, while the second bearing 328 is a journal bearing. In other embodiments, the first bearing 326 may be a journal bearing, while the second bearing 328 is a ball bearing. In other embodiments, both bearings 326 and 328 may be ball bearings or journal bearings. According to embodiments, the outer diameter of the bearings 326 and 328 are configured such that the bearings can be coupled to the inside surface 324 of the housing 304, allowing the drive shaft 308 to rotate within the housing 304.

As is further shown in FIG. 3, the motor 302 may further include a first flux return disc 330 disposed between the first bearing 326 and the rotors and the stators; and a second flux return disc 332 may be disposed between the second bearing 328 and the rotors and the stators. The flux return discs may be made of any material configured to protect the adjacent bearings from magnetic interaction, as well as to focus the magnetic field lines through the adjacent rotor and/or stator, thereby facilitating increasing power and efficiency of the motor 302. In embodiments, for example, each flux return disc 330 and 332 may be made of a Hiperco alloy and may have an outer diameter approximately equal to the outer diameter of the bearings 326 and 328 and the stators 314.

The illustrative circulatory support device 300 and motor 302 shown in FIG. 3, and the illustrative stator 400 shown in FIG. 4, are not intended to suggest any limitation as to the scope of use or functionality of embodiments of the present disclosure. The illustrative circulatory support device 300, motor 302, and stator 400 also should not be interpreted as having any dependency or requirement related to any single component or combination of components illustrated therein. Additionally, various components depicted in FIGS. 3 and 4 may be, in embodiments, integrated with various ones of the other components depicted therein (and/or components not illustrated), all of which are considered to be within the ambit of the present disclosure.

Figure 5:
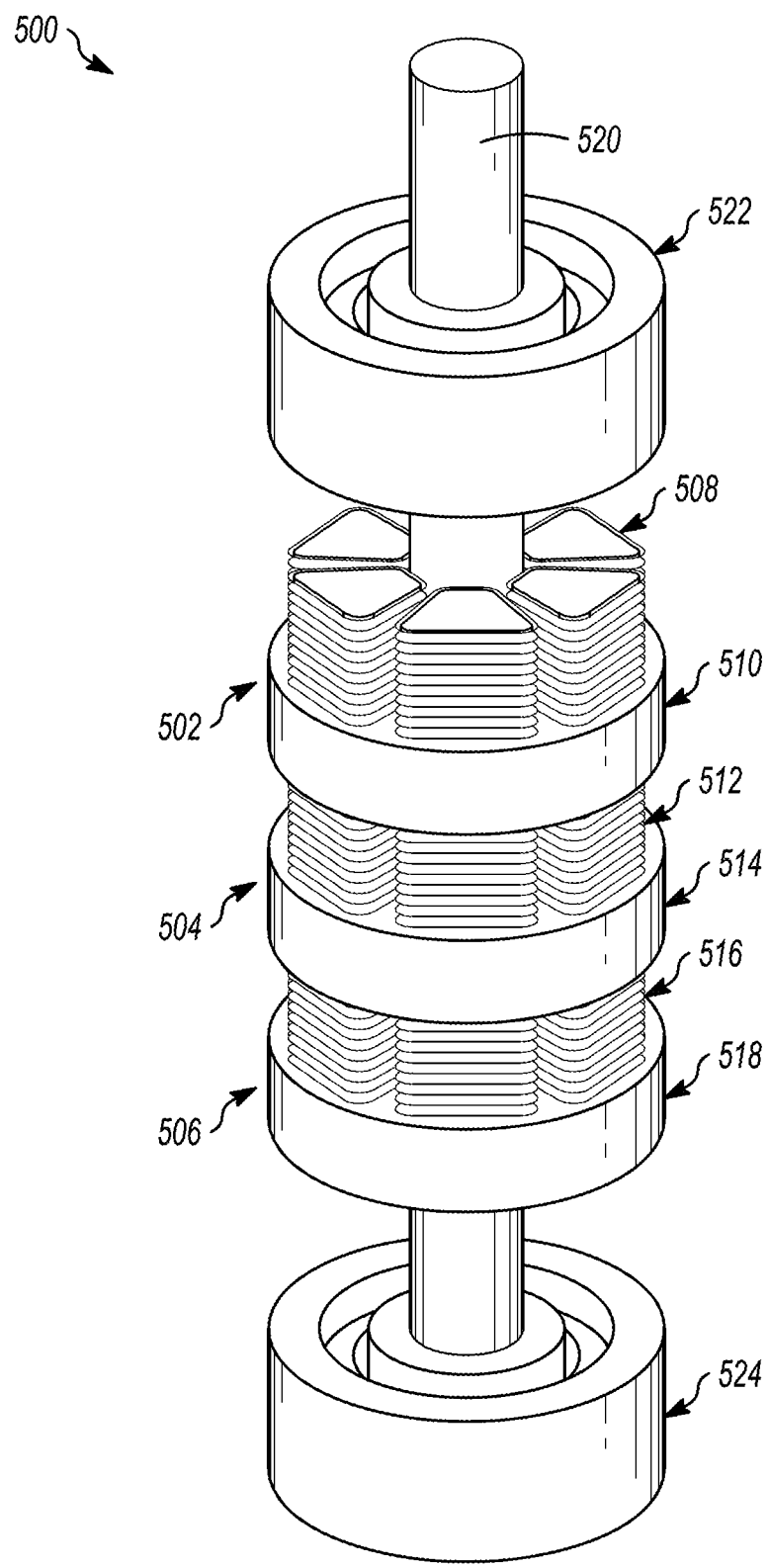
FIG. 5 is a perspective view of a portion of an axial flux motor, with its housing removed, showing an illustrative arrangement of rotors and stators, in accordance with embodiments of the subject matter disclosed herein.

FIG. 5 is a perspective view of a portion of an axial flux motor 500, with its housing removed, showing an illustrative arrangement of rotors and stators, in accordance with embodiments of the subject matter disclosed herein. According to embodiments, the illustrative motor 500 may be, be similar to, or include the motor 102 depicted in FIG. 1 and/or the motor 302 depicted in FIG. 3. As shown, the motor 500 includes three rotor/stator pairs 502, 504, and 506, each including, respectively, a rotor 508, 512, and 516; and a stator 510, 514, and 518. A drive shaft 520 extends through all of the rotors and stators and is rotatably supported by a pair of bearings 522 and 524. According to embodiments, the motor 500 may include a flux return disc (not shown) disposed between each bearing 522 and 524 and the rotor/stator pairs.

According to embodiments, the motor 500 may be configured to include any number of rotor/stator pairs. In embodiments, the motor 500 may be dynamically configurable such that, for example, if additional power is needed for a particular application, additional rotor/stator pairs can be added. Additionally, in embodiments, although the motor 500 is depicted as having stators without stator cores, one or more of the stators may include a stator core.

The illustrative motor 500 shown in FIG. 5 is not intended to suggest any limitation as to the scope of use or functionality of embodiments of the present disclosure. The illustrative motor 500 also should not be interpreted as having any dependency or requirement related to any single component or combination of components illustrated therein. Additionally, various components depicted in FIG. 5 may be, in embodiments, integrated with various ones of the other components depicted therein (and/or components not illustrated), all of which are considered to be within the ambit of the present disclosure.

Figure 6A:
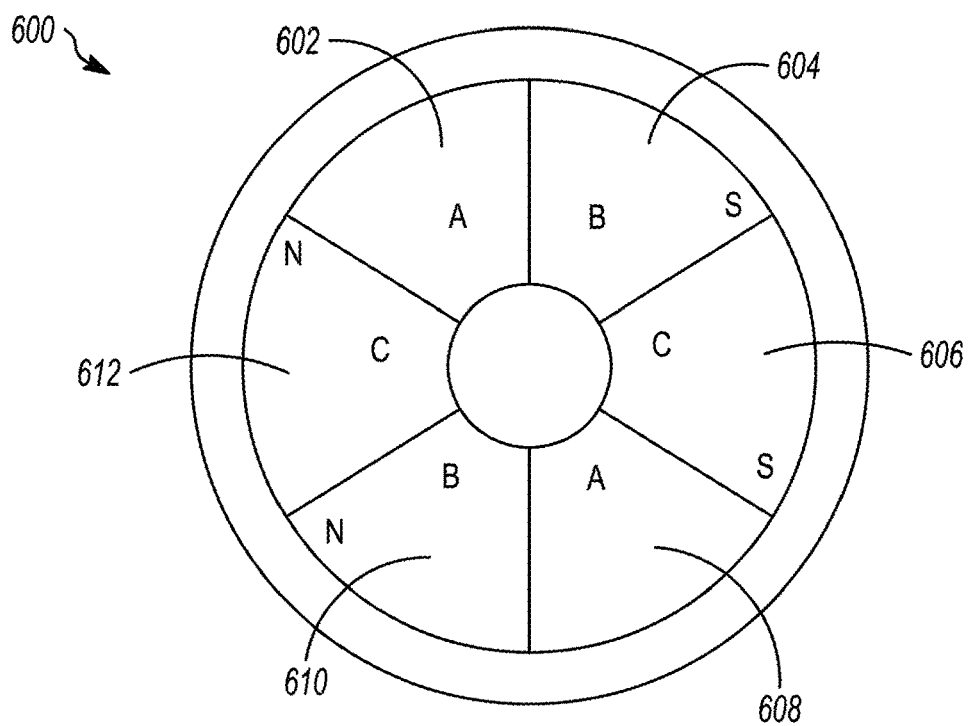
FIGS. 6A and 6B are schematic drawings depicting an illustrative operation of components of an axial flux motor, in accordance with embodiments of the subject matter disclosed herein.
Figure 6B:
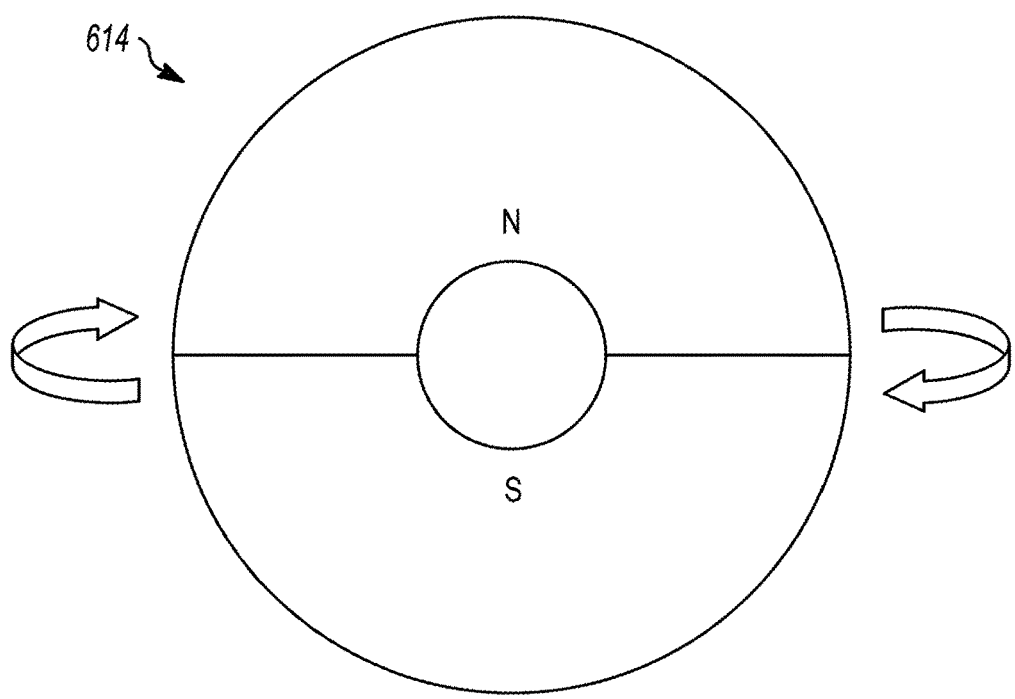

FIGS. 6A and 6B are schematic drawings depicting an illustrative operation of components of an axial flux motor, in accordance with embodiments of the subject matter disclosed herein. The axial flux motor may be, be similar to, include, or be included in, the axial flux motor 102 depicted in FIG. 1, the axial flux motor 302 depicted in FIG. 3, and/or the axial flux motor 502 depicted in FIG. 5. FIG. 6A is a schematic diagram of an illustrative stator 600 having a first winding 602, a second winding 604, a third winding 606, a fourth winding 608, a fifth winding 610, and a sixth winding 612, disposed around a drive shaft 614. According to embodiments, a controller (e.g., the controller 106 depicted in FIG. 1 or the controller 306 depicted in FIG. 3) may be operably coupled to the stator 600, as well as any other stators of the motor.

In embodiments, the controller may be configured to activate, during a startup procedure, all of the stators; and then, deactivate, upon determining that the motor has a specified operating condition (e.g., a specified amount of torque, a specified angular velocity, etc.), one or more of the stators. In this manner, the controller may be configured to facilitate saving energy by only activating the number and arrangement of stators necessary to produce the amount of torque required to perform a specified operation. Additionally or alternatively, the controller may be configured to activate certain stators and/or combinations of stators to provide specified amounts of torque at specified locations along the drive shaft, and/or the like.

According to embodiments, for a given stator (e.g., the stator 600 depicted in FIG. 6A), the windings may be paired as shown. That is, for example, the first winding 602 may be paired with the fourth winding 608 to create a first pair (labeled "A"), the second winding 604 may be paired with the fifth winding 610 to create a second pair (labeled "B"), and the third winding 606 may be paired with the sixth winding 612 to create a third pair (labeled "C"). The windings of each pair may be polarized with respect to one another (e.g., where one winding is polarized to North (N) and the other is approximately simultaneously polarized to South (S)) according to a sequence to cause one or more adjacent rotors to rotate.

For example, according to embodiments, to produce torque, the winding pairs are turned on in a specified sequence, creating an electromagnet that is attracted to the permanent magnet in the rotor 614 (depicted in FIG. 6B), causing the rotor 614 to rotate. An example of a sequence may include, for example, beginning with the winding pair A turned off, while the winding pairs B and C are turned on, causing the windings 604 and 606 to be polarized to S and the windings 610 and 612 to be polarized to N, thereby causing the rotor 614 to rotate, as depicted. Next, the winding pair B may be turned off, while the winding pair C remains on and the winding pair A is turned on, such that windings 602 and 612 become polarized to N, while the windings 606 and 608 become polarized to S. According to embodiments, any number of different sequences and/or patterns of turning off and on windings to polarize various aspects of the stator 600 may be employed to facilitate causing the rotor 614 to rotate in a desired direction with a desired amount of torque.

The illustrative operation shown in FIGS. 6A and 6B is not intended to suggest any limitation as to the scope of use or functionality of embodiments of the present disclosure. The illustrative operation also should not be interpreted as having any dependency or requirement related to any single component or combination of components illustrated therein. Additionally, various components depicted in FIGS. 6A and 6B may be, in embodiments, integrated with various ones of the other components depicted therein (and/or components not illustrated), all of which are considered to be within the ambit of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. An axial flux motor, comprising:
a housing;
a drive shaft disposed within the housing;
at least one rotor having a diameter from 0.5 mm to 20 mm, the at least one rotor comprising a diametrically-magnetized single pole pair magnetic ring having a rotor aperture defined through the center of the magnetic ring, wherein the drive shaft extends through the rotor aperture and wherein the at least one rotor is fixed to the drive shaft;
at least one stator, the at least one stator comprising a plurality of conductive windings and a stator aperture, wherein the drive shaft extends through the stator aperture and wherein the drive shaft is rotatable within the aperture, and wherein the at least one stator is configured to generate an axial magnetic field that causes the at least one rotor to rotate, thereby rotating the drive shaft;
a first bearing rotatably coupled to the drive shaft;
a second bearing rotatably coupled to the drive shaft, such that the at least one rotor and the at least one stator are disposed between the first bearing and the second bearing:
a first flux return disc disposed between the first bearing and the at least one rotor and the at least one stator; and
a second flux return disc disposed between the second bearing and the at least one rotor and the at least one stator;
wherein the motor is configured to drive an impeller of a percutaneous mechanical circulatory support device, wherein the impeller is coupled to the drive shaft.

2. The motor of claim 1, the at least one stator comprising a plurality of stators, wherein each of the plurality of stators is configured to cause at least one adjacent rotor to rotate.

3. The motor of claim 1, the at least one stator comprising a slotted stator core, wherein each of the plurality of conductive windings is wound around one or more slots of the stator core.

4. The motor of claim 1, wherein each of the windings is approximately wedge-shaped, having a first width at a first end, adjacent the drive shaft, and a second width at a second end, wherein the second width is greater than the first width.

5. The motor of claim 1, wherein each of the first and second flux return discs is made of a Hiperco alloy.

6. The motor of claim 1, wherein each of the plurality of windings is printed on a printed circuit board or 3D printed.

7. An axial flux motor, comprising:
a housing;
a drive shaft disposed within the housing;
at least one rotor having a diameter from 0.5 mm to 20 mm, the at least one rotor comprising a diametrically-magnetized single pole pair magnetic ring having a rotor aperture defined through the center of the magnetic ring, wherein the drive shaft extends through the rotor aperture and wherein the at least one rotor is fixed to the drive shaft; and
at least one stator, the at least one stator comprising a plurality of conductive windings arranged around the drive shaft and a stator aperture, wherein the drive shaft extends through the stator aperture and wherein the drive shaft is rotatable within the aperture, wherein the at least one stator does not include a stator core, and wherein the at least one stator is configured to generate an axial magnetic field that causes the at least one rotor to rotate, thereby rotating the drive shaft;
a first bearing rotatably coupled to the drive shaft;
a second bearing rotatably coupled to the drive shaft, such that the at least one rotor and the at least one stator are disposed between the first bearing and the second bearing;
a first Hiperco alloy flux return disc disposed between the first bearing and the at least one rotor and the at least one stator; and
a second Hiperco alloy flux return disc disposed between the second bearing and the at least one rotor and the at least one stator;
wherein the motor is configured to drive an impeller of a percutaneous mechanical circulatory support device, wherein the impeller is coupled to the drive shaft.

8. The motor of claim 7, wherein each of the plurality of conductive windings is coupled to an inside surface of the housing.

9. The motor of claim 7, wherein each of the plurality of windings is approximately wedge-shaped, having a first width at a first end, adjacent the drive shaft, and a second width at a second end, and wherein the second width is greater than the first width.

10. A percutaneous mechanical circulatory support device, comprising:
a housing;
a drive shaft disposed within the housing;
an impeller configured to be driven by the drive shaft;
a plurality of rotors each having a diameter from 0.5 mm to 20 mm, each of the plurality of rotors comprising a diametrically-magnetized single pole pair magnetic ring having a rotor aperture defined through the center of the magnetic ring, wherein the drive shaft extends through the rotor aperture and wherein the rotor is fixed to the drive shaft; and
a plurality of stators, each stator of the plurality of stators comprising a plurality of conductive windings and a stator aperture, wherein the drive shaft extends through the stator aperture and wherein the drive shaft is rotatable within the aperture, and wherein each stator of the plurality of stators is configured to generate an axial magnetic field that causes at least one adjacent rotor of the plurality of rotors to rotate, thereby rotating the drive shaft and the impeller;
a first bearing rotatably coupled to the drive shaft;
a second bearing rotatably coupled to the drive shaft, such that the plurality of rotors and the plurality of stators are disposed between the first bearing and the second bearing;
a first Hiperco alloy flux return disc disposed between the first bearing and the plurality of rotors and the plurality of stators; and
a second Hiperco alloy flux return disc disposed between the second bearing and the plurality of rotors and the plurality of stators.

11. The circulatory support device of claim 10, further comprising a controller operably coupled to the motor and configured to:
- activate, during a startup procedure, the plurality of stators; and
- deactivate, upon determining that the motor has a specified operating condition, one or more of the plurality of stators.

12. The motor of claim 10, the stator comprising a slotted stator core, wherein each of the plurality of conductive windings is wound around one or more slots of the stator core.

13. The motor of claim 10, wherein the stator does not include a stator core, and wherein each of the plurality of conductive windings is coupled to an inside surface of the housing.

14. The motor of claim 10, wherein each of the windings is approximately wedge-shaped, having a first width at a first end, adjacent the drive shaft, and a second width at a second end, wherein the second width is greater than the first width.

15. The motor of claim 10, wherein each of the plurality of windings is printed on a printed circuit board or 3D printed.

\* \* \* \* \*